(12) United States Patent
Chotani et al.

(10) Patent No.: US 8,012,713 B2
(45) Date of Patent: Sep. 6, 2011

(54) ENZYME PRODUCTION IN CULTURE MEDIUM COMPRISING RAW GLYCEROL

(75) Inventors: Gopal K. Chotani, Cupertino, CA (US); Kenneth F. Herfert, Belmont, CA (US); Janine Reimann, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 12/521,849

(22) PCT Filed: Jan. 10, 2008

(86) PCT No.: PCT/US2008/050735
§ 371 (c)(1), (2), (4) Date: Oct. 16, 2009

(87) PCT Pub. No.: WO2008/086466
PCT Pub. Date: Jul. 17, 2008

(65) Prior Publication Data
US 2010/0297696 A1    Nov. 25, 2010

Related U.S. Application Data

(60) Provisional application No. 60/879,904, filed on Jan. 11, 2007.

(51) Int. Cl.
*C12P 21/06* (2006.01)
(52) U.S. Cl. ...................................... 435/69.1
(58) Field of Classification Search .................. 435/69.1
See application file for complete search history.

(56) References Cited

U.S. PATENT DOCUMENTS

| | | |
|---|---|---|
| 3,971,856 A | 7/1976 | Daftary |
| 4,610,965 A | 9/1986 | Johnson et al. |
| 5,310,665 A | 5/1994 | Lambeir et al. |
| 5,360,732 A | 11/1994 | Berka et al. |
| 5,384,257 A | 1/1995 | Lambeir et al. |
| 7,135,309 B1 | 11/2006 | Laffend et al. |

FOREIGN PATENT DOCUMENTS

| | | |
|---|---|---|
| WO | WO 95/04134 A1 | 2/1995 |
| WO | WO 2004/035070 A1 | 4/2004 |
| WO | WO 2005/087918 A2 | 9/2005 |
| WO | WO 2006/071598 A1 | 7/2006 |

OTHER PUBLICATIONS

Arbige, M.V. et al. "Fermentation of *Bacillus*." In *Bacillus subtilis and other Gram-positive bacteria: biochemistry physiology and molecular genetics*, edited by A.L. Sonenshein et al., pp. 871-895. Washington, D.C.: American Society for Microbiology, 1993.
Aunstrup, K. "Industrial Production of Proteolytic Enzymes." In *Industrial Aspects of Biochemistry*, edited by B. Spencer, vol. 30, Part I: pp. 23-46. Amsterdam, NL: Elsevier, 1974.
Cote, R.J. et al. "Nutrition and Media." In *Methods for General and Molecular Bacteriology*, edited by P. Gerhardt et al., p. 158. Washington, D.C.: ASM Press, 1994.
Davis, R.N. et al. "Genetic and microbiological research techniques for *Neurospora crassa*." *Methods Enzymol* 17A: 79-143, 1970.
Estell, D.A. et al. "Engineering an enzyme by site-directed mutagenesis to be resistant to chemical oxidation." *J. Biol. Chem.* 260(11): 6518-6521, Jun. 10, 1985.
Ferrari, E. et al. "Commercial Production of Extracellular Enzymes." In *Bacillus subtilis and other Gram-positive bacteria: biochemistry physiology and molecular genetics*, edited by A.L. Sonenshein et al., pp. 917-937. Washington, D.C.: American Society for Microbiology, 1993.
Ilmen, M. et al. "Regulation of cellulase gene expression in the filamentous fungus *Trichoderma reesei*." *Appl. Environ. Microbiol.* 63(4): 1298-1306, Apr. 1, 1997.
Kelly, J.M. et al. "Transformation of *Aspergillus niger* by the amdS gene of *Aspergillus nidulans*." *The EMBO Journal* 4(2): 475-479, Feb. 1985.
Kim, J.-W. et al. "High Cell Density Culture of *Yarrowia lipolytica* Using a One-Step Feeding Process." *Biotechnology Progress* 16(4): 657-660, 2000.
O'Herrin, S.M. et al. "Expression of human recombinant [beta]2-microglobulin by *Aspergillus nidulans* and its activity." *Human Immunology* 51(2): 63-72, Dec. 1996.
Paloheimo, M. et al. "High-Yield Production of a Bacterial Xylanase in the Filamentous Fungus *Trichoderma reesei* Requires a Carrier Polypeptide with an Intact Domain Structure." *Appl. Environ. Microbiol.* 69(12): 7073-7082, Dec. 1, 2003.
Papanikolaou, S. et al. "Lipid production by *Yarrowia lipolytica* growing on industrial glycerol in a single-stage stage continuous culture." *Bioresource Technology* 82(1): 43-49, Mar. 2002.
Parro, V. et al. "Overproduction and purification of an agarase of bacterial origin." *Journal of Biotechnology* 58(1): 59-66, Oct. 2, 1997.
Penttilä, M. et al. "A versatile transformation system for the cellulolytic filamentous fungus *Trichoderma reesei*." *Gene* 61(2): 155-164, 1987.
Saarelainen, R. et al. "Expression of Barley Endopeptidase B in *Trichoderma reesei*." *Appl. Environ. Microbiol.* 63(12): 4938-4940, Dec. 1, 1997.
Ward, M. et al. "Characterization of Humanized Antibodies Secreted by *Aspergillus niger*." *Appl. Environ. Microbiol.* 70(5): 2567-2576, May 1, 2004.
Ward, M. et al. "Improved Production of Chymosin in *Aspergillus* by Expression as a Glucoamylase-Chymosin Chymosin Fusion." *Nat Biotech* 8(5): 435-440, May 1990.
Westers, L. et al. "Secretion of functional human interleukin-3 from *Bacillus subtilis*." *Journal of Biotechnology* 123(2): 211-224, May 17, 2006.
Yang, H. et al. "Expression and characterization of a heterodimer of *Streptomyces chromofuscus* phospholipase D." *Biochimica et Biophysica Acta (BBA)—Proteins & Proteomics* 1703(1): 43-51, Dec. 1, 2004.

*Primary Examiner* — Maryam Monshipouri

(57) ABSTRACT

The present invention is directed to a method of producing desired proteins from a host cell grown in a media comprising raw glycerol as a carbon source.

11 Claims, 7 Drawing Sheets

*Streptomyces lividans* fed-batch culture - cell growth

*Streptomyces lividans* fed-batch culture - enzyme production

Hansenula polymorpha batch culture - cell growth

Hansenula polymorpha batch culture - enzyme production

ENZYME PRODUCTION IN CULTURE MEDIUM COMPRISING RAW GLYCEROL

CROSS-REFERENCE TO RELATED APPLICATIONS

This application is a 371 of PCT/US2008/050735, filed Jan. 10, 2008, which claims the benefit of U.S. Provisional Application No. 60/879,904, filed on Jan. 11, 2007, which is hereby incorporated be reference herein in its entirety.

FIELD OF THE INVENTION

The invention relates to use of raw glycerol as a carbon source for growth of cells in culture, and production of proteins in such cell cultures.

BACKGROUND

In certain molecular biotechnology methods cells are grown in culture media and used to produce desired proteins. The desired protein that is produced may be recovered and used in a variety of industrial and medical applications. For example, the desired protein may be used as a therapeutic protein such as an antibody or an enzyme and used in industrial applications, such as cleaning applications (e.g., laundry detergents), paper-making applications, animal feed applications, baking applications, methods for starch hydrolysis and other methods that require large amounts of a particular enzyme.

Producing large amounts of protein using recombinant cells or non-recombinant cells, frequently requires that cells be cultured in a medium containing a carbon source, a nitrogen source, and other nutrients e.g., amino acids, vitamins, minerals, etc., required for growth of those cells. Many cell cultures incorporate glucose or a combination of glucose and other substrates as a carbon source in the cell culture or as a substrate feed in the cell culture.

This invention relates to an alternative carbon source for use in cell cultures. The inventors herein have discovered that the addition of raw glycerol to a nutrient media either as the sole carbon source or in combination with other sugars (e.g., glucose) may be used as a carbon source for the production of desired proteins by cells grown in the cultures. The use of raw glycerol in the culture of cells would be of great commercial benefit.

BRIEF SUMMARY OF THE INVENTION

A culture medium containing raw glycerol is provided. In certain embodiments, the raw glycerol may be the sole carbon source of the medium. In other embodiments, the culture medium may contain, in addition to raw glycerol, one or more secondary carbon sources such as 6 carbon sugars including but not limited to glucose, galactose, fructose, sorbose and mannose or a combination of 6 carbon sugars such as glucose and fructose (sucrose), cellulose, lactose and the like. In other embodiments, the culture medium may contain, in addition to raw glycerol, one or more secondary carbon sources, such as protein sources (e.g., soy and/or corn).

A cell culture comprising the subject raw glycerol-containing culture medium is provided. In certain embodiments, the cell culture comprises: a plurality of cells which in particular embodiments may comprise a recombinant nucleic acid for producing a desired protein, and a culture medium comprising raw glycerol. In certain embodiments, the cells of the cell culture may be bacterial cells or fungal cells. The recombinant nucleic acid may contain an expression cassette comprising, in operable linkage: a) a promoter region, b) a coding region encoding a desired protein; and c) a terminator region.

The protein produced by the recombinant cells may be native to the cells or heterologous to cells and, in certain embodiments, the protein may be intracellular or secreted from the cells into the culture medium. The protein for example, may be an industrial enzyme, a therapeutic protein, a reporter protein, a selectable marker, a food additive or a foodstuff.

Also provided is a protein production method. In general terms, this method comprises maintaining the above-described cell culture to provide for production of a desired protein. In certain cases, the protein may be recovered from the culture medium.

The above-described raw glycerol-containing culture medium may be produced by combining, e.g., mixing, raw glycerol with other components required for cell growth, e.g., a nitrogen source, and other nutrients, and water.

In some embodiments, the above-described cell culture may be produced by combining, e.g., mixing: a) raw glycerol and b) a culture of cells comprising a nucleic acid (e.g. a recombinant nucleic acid) for producing the desired protein. In other embodiments, the above-described cell culture may be produced by combining (e.g., inoculating) a cell culture medium comprising raw glycerol with cells that comprise a recombinant nucleic acid for producing the protein. The culture methods may be batch, fed-batch, or continuous culture methods.

DETAILED DESCRIPTION

Definitions

Figure 1:
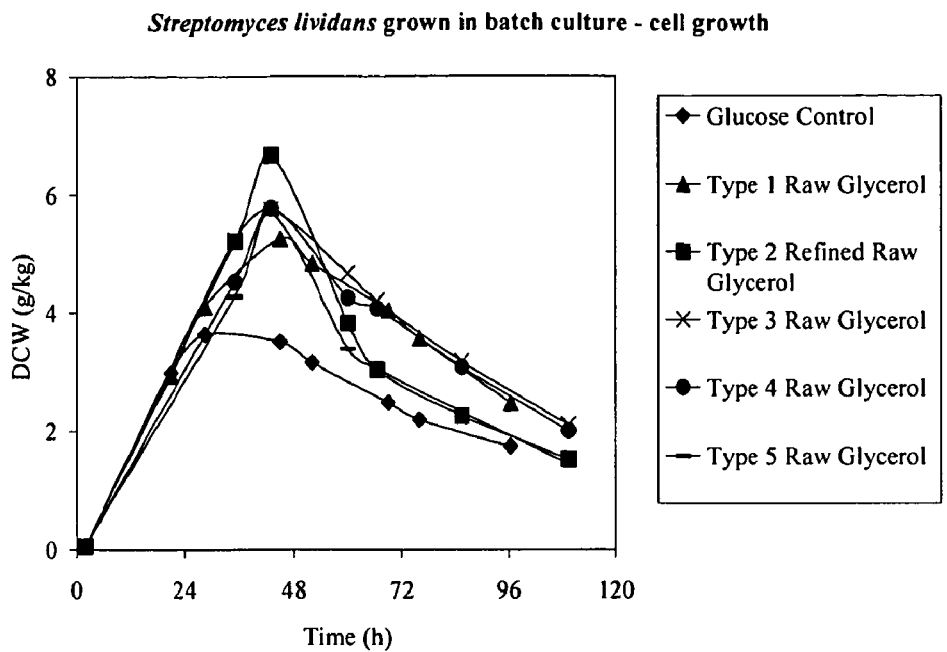
FIG. 1 depicts the cell mass of recombinant *Streptomyces lividans* cells grown in batch culture over time (DCW; grams of cells/kg), cultured in media containing raw glycerol or glucose, as described in Example 1.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with general dictionaries of many of the terms used in this invention. Also reference is made to Atkinson et al., Biochemical Engineering and Biotechnology Handbook, $2^{nd}$ Ed, Stockton Press (1991) as a general reference. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

"Glycerol" refers to ($C_3H_8O_3$) 1,2,3-propane, also known as 1,2,3-Trihydroxypropane. The term is also used interchangeability with "glycerin" and "glycerine".

The term "raw glycerol" is defined herein as an aqueous solution having a % purity of less than 99% (v/v), e.g., at least 25% and less than 95% glycerol (v/v), 95% to 98% glycerol (v/v), 95% to 99% glycerol (v/v), or 98% to 99% glycerol (v/v).

The term "refined glycerol" as used herein means "raw glycerol" having less than 1% of salt (w/v).

The term "distilled glycerol" is defined herein as an aqueous solution having a % purity of 95% or greater glycerol (v/v) (greater than about 95% and up to 100% glycerol (v/v)).

The term "culture medium" is defined herein as a man-made composition, either liquid or solid, that contains a carbon source, a nitrogen source, and other nutrients, e.g., amino acids, vitamins, minerals, etc., required for culture of cells. A culture medium does not contain cells. A culture medium may be inoculated with cells to produce a cell culture that contains cells and the culture medium.

The terms "cell culture" and "culture of cells" are used interchangeably to describe a liquid composition containing living cells, typically of a single type, and a culture medium. Cell cultures may be made by inoculating a culture medium with cells. The cells of a cell culture are metabolically active, however, they may or may not be actively growing or dividing. A cell culture exists in vitro.

The term "batch" describes a batch cell culture to which substrate, in either solid or concentrated liquid form, is added initially at the start of a fermentation run. A batch culture is initiated by inoculating cells to the culture medium with no subsequent inflow of nutrients. The concentrations of the nutrients and metabolites in the culture medium are dependent upon the initial concentrations within the batch and the subsequent alteration of the compositions of the nutrient feed due to the act of cellular fermentation. The term "fed-batch" describes a batch cell culture to which substrate, in either solid or concentrated liquid form, is added either periodically or continuously during a fermentation run. A fed-batch culture is initiated by inoculating cells to the medium, but there is a subsequent inflow of nutrients such as by a concentrated nutrient feed. However, there is no systematic removal of cultural fluid or cells.

The term "continuous cell culture" or continuous culture" means a culture characterized by both a continuous inflow of a liquid nutrient feed and a continuous liquid outflow.

The term "vessel" means any suitable container for culturing cells, including but not limited to vats, bottles, flasks, bags, bioreactors, and any other suitable receptacle for conducting the methods of the present invention.

The term "promoter" is defined herein as a nucleic acid that directs transcription of a downstream polynucleotide in a cell. In certain cases, the polynucleotide may contain a coding sequence and the promoter may direct the transcription of the coding sequence into translatable RNA.

The term "isolated" as defined herein means a compound, a protein, cell, nucleic acid sequence or amino acid that is removed from at least one component with which it is naturally associated The term "coding sequence" is defined herein as a nucleic acid that, when placed under the control of appropriate control sequences including a promoter, is transcribed into mRNA which can be translated into a polypeptide. A coding sequence may contain a single open reading frame, or several open reading frames separated by introns, for example. A coding sequence may be cDNA, genomic DNA, synthetic DNA or recombinant DNA, for example. A coding sequence generally starts at a start codon (e.g., ATG) and ends at a stop codon (e.g., UAA, UAG and UGA).

The term "recombinant" refers to a polynucleotide or polypeptide that does not naturally occur in a host cell. A recombinant molecule may contain two or more naturally occurring sequences that are linked together in a way that does not occur naturally.

The term "heterologous" refers to elements that are not normally associated with each other. For example, a if a recombinant host cell produces a heterologous protein, that protein is not produced in a wild-type host cell of the same type, a heterologous promoter is a promoter that is not present in nucleic acid that is endogenous to a wild type host cell, and a promoter operably linked to a heterologous coding sequence is a promoter that is operably linked to a coding sequence that it is not usually operably linked to in a wild-type host cell.

The term "operably linked" refers to an arrangement of elements that allows them to be functionally related. For example, a promoter is operably linked to a coding sequence if it controls the transcription of the sequence, and a signal sequence is operably linked to a protein if the signal sequence directs the protein through the secretion system of a host cell.

The term "nucleic acid" encompasses DNA, RNA, single or doubled stranded and modification thereof. The terms "nucleic acid" and "polynucleotide" may be used interchangeability herein.

The term "DNA construct" as used herein means a nucleic acid sequence that comprises at least two DNA polynucleotide fragments.

As used herein, the term "reporter" refers to a protein that is easily detected and measured. In certain cases, a reporter may be optically detectable, e.g., fluorescent, luminescent or colorigenic.

As used herein, the term "selectable marker" refers to a biopolymer, either a polypeptide or polynucleotide that allows host cells that contain the biopolymer to be selected over other cells that do not contain the biopolymer. Selectable markers provide resistance to toxic compounds such as antibiotics, herbicides, and the like.

The term "signal sequence" or "signal peptide" refers to a sequence of amino acids at the N-terminal portion of a protein, which facilitates the secretion of the mature form of the protein outside the cell. The mature form of the extracellular protein lacks the signal sequence which is cleaved off during the secretion process.

The term "vector" is defined herein as a polynucleotide designed to carry nucleic acid sequences to be introduced into one or more cell types. Vectors include cloning vectors, expression vectors, shuttle vectors, plasmids, phage or virus particles, DNA constructs, cassettes and the like. Expression vectors may include regulatory sequences such as promoters, signal sequences, coding sequences and transcription terminators.

An "expression vector" as used herein means a DNA construct comprising a coding sequence that is operably linked to suitable control sequences capable of effecting expression of a protein in a suitable host. Such control sequences may include a promoter to effect transcription, an optional operator sequence to control transcription, a sequence encoding suitable ribosome binding sites, enhancers and sequences which control termination of transcription and translation.

As used herein, the terms "polypeptide" and "protein" are used interchangeably and include reference to a polymer of any number of amino acid residues. The terms apply to amino acid polymers in which one or more amino acid residue is an artificial chemical analog of a corresponding naturally occurring amino acid, as well as to naturally occurring amino acid polymers. The terms also apply to polymers containing conservative amino acid substitutions such that the polypeptide remains functional. "Peptides" are polypeptides having less than 50 amino acid residues.

A "host cell" refers to a suitable host for an expression vector comprising a DNA construct encoding a desired protein. A host cell may be any cell type.

The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, glucans, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic.

A "non-pathogenic" strain is a strain that is not pathogenic to humans.

Culture Media

As noted above, a culture medium containing raw glycerol is provided. The culture medium may contain a nitrogen source, raw glycerol, and other nutrients, e.g., amino acids, vitamins, minerals, etc., required for culture of cells. The raw glycerol may be used as a carbon source by cells growing in the culture medium.

In certain embodiments, the culture medium may comprise a further source of carbon, e.g., a sugar, for growth of the cells. Accordingly, in certain embodiments, raw glycerol may be the sole carbon source for the cells. In other embodiments, the raw glycerol may be present with one or more other secondary carbon sources for the cells.

In exemplary embodiments, raw glycerol in the culture medium may have a percent glycerol purity of 25% to 85% (v/v); also 25% to 50% (v/v); also 50% to 75% (v/v); also 75% to 85% (v/v); also 85% to 90% (v/v), or also 90% to less than 95% (v/v). In some embodiments, the raw glycerol may have a glycerol purity of 95% to 98% (v/v). In some embodiments, the raw glycerol may have a glycerol purity of less than 99% (v/v).

In certain embodiments, raw glycerol may contain salt (e.g., KCl or NaCl; sodium or potassium sulfate, phosphate, or nitrate) at a concentration of up to 12% (w/v), e.g., in the range of 1% to 10% (w/v); 1% to 5% (w/v); 5% to 8% (w/v) or 8% to 12% (w/v). Refined glycerol contains less than 1% of salt (w/v), e.g., salt at a concentration in the range of 0.01% to 0.1% (w/v), 0.1% to 0.5% (w/v) or 0.5% to less than 1% (w/v). In one embodiment, the raw glycerol comprises substantially no salt (0 to 0.01%, or 0 to 0.001%, salt).

While in preferred embodiments, raw glycerol is used in the culture media and cell culture, distilled glycerol may be used in certain embodiments. In some embodiments, distilled glycerol, which is defined as having a purity of 95% or greater, may have a purity of at least 95% and less than 99.5% (v/v), e.g., greater than 95% to 97% glycerol (v/v), 97% to 99% glycerol (v/v) or 99% to less than 99.5% glycerol (v/v). In some embodiments, the distilled glycerol which is used in the methods encompassed by the invention will have a purity of at least 99.5%, e.g., of at least 99.6%, at least 99.7%, or at least 99.9% glycerol (v/v). Glycerol having a % purity within the above defined ranges may be referred to as technical grade glycerol (e.g., greater than 95% to less than 99.5%) and pharmaceutical grade glycerol (e.g., at least 99.5% glycerol to at least 99.9% glycerol (v/v).

The amount of raw glycerol present in a culture medium may vary greatly depending on growth methods used, e.g., whether the cells are grown in batch culture (for example, in a shaker flask), continuous culture, or fed-batch culture. In certain embodiments, the culture medium may comprise 0.1% to 75% raw glycerol (v/v), e.g., 0.5% to 2% raw glycerol (particularly if the cell culture is grown under continuous or fed-batch methods in which the carbon source is rapidly used by cells cultured in the medium, 2% to 5% raw glycerol, 5% to 10% raw glycerol, 10% to 30% raw glycerol, 30% to 50% raw glycerol or 50% to 75% raw glycerol. In some embodiments, the raw glycerol concentration is any of about 0.1, 0.5, 1, 5, 10, 15, 20, or 25% (v/v) to about of about 50, 55, 60, 65, 70, 75, or 80% (v/v). In some embodiments, the cells are grown in a batch fermentation process, and the culture medium comprises about 1% to about 5% raw glycerol (v/v). In some embodiments, the cells are grown in a fed-batch fermentation process and the culture medium comprises about 20% to about 50% raw glycerol (v/v).

If a secondary carbon source is present in the culture medium, the secondary carbon source may be a sugar, e.g., glucose, galactose, fructose, maltose, xylose, arabinose, dextrose or sucrose, etc. If a secondary carbon source is present in the culture medium, the secondary carbon source and the raw glycerol may be present at a relative molar concentration in the range of 1:99 (e.g., 1 molecule of the secondary carbon source to 99 molecules of glycerol) to 99:1 (e.g., 99 molecules of the secondary carbon source to 1 molecule of glycerol). For example, the secondary carbon source and the raw glycerol may be present at a relative molar concentration in the range of 1:99 to 1:10, 1:10 to 1:2, 1:2 to 2:1, 10:1 to 2:1, or 10:1 to 99:1, for example. In some preferred embodiments, the secondary carbon source will be glucose and in particular when a cell culture comprises fungal cells some glucose will be provided as a carbon source. In some preferred embodiments the ratio of raw glycerol to glucose will be in the range of 1:4 to 4:1 and also 2:1 to 1:2.

The identity and suitable concentrations of other components that may be employed in the subject cell culture medium, e.g., the nitrogen source and other nutrients, etc., generally depend on the type of cells being grown in the culture medium. Such components are generally well known in the art (see, e.g., Ausubel, et al, Short Protocols in Molecular Biology, 3rd ed., Wiley & Sons, 1995; Sambrook, et al., Molecular Cloning: A Laboratory Manual, Second Edition, 1989 Cold Spring Harbor, N.Y.; Talbot, Molecular and Cellular Biology of Filamentous Fungi: A Practical Approach, Oxford University Press, 2001; Kinghorn and Turner, Applied Molecular Genetics of Filamentous Fungi, Cambridge University Press, 1992; and *Bacillus* (Biotechnology Handbooks) by Colin R. Harwood, Plenum Press, 1989; *Bacillus subtilis*: From Genes to Cells, Sonenshein, A. L., Hoch, J. A. and Losick, R ASM (2001), as well as e.g., Ilmen et al., Appl. Environ. Microbiol. 1997 63:1298-1306; O'Herrin et al. Hum. Immunol. 1996 51:63-72; Westers et al., J. Biotechnol. 2006 123:211-24 and Yang et al., Biochim Biophys. Acta 2004 1703:43-51). Culture conditions for a given cell type may also be found in the scientific literature and/or from the source of the fungi such as the American Type Culture Collection (ATCC) and Fungal Genetics Stock Center.

Exemplary components that may be employed in culture media include, but are not limited to: an extract from microbial, animal or plant cells, e.g., soymeal, soy protein, soy concentrate, corn steep, corn meal, corn gluten, yeast extract, soy flour, cotton meal, peanut meal, potato protein, whey, fish meal, bacto-tryptone, bacto-peptone, etc., salts, e.g., $KH_2PO_4$, $MgSO_4$, $CaCl_2$, NaCl, $FeCl_3$, $MgCl_2$, $MnCl_2$, other compounds, e.g., thiamine chloride, biotin, vitamin B12, $NaH_2PO_4H_3BO_3$, $ZnSO_4$, $Na_2MoO_4$ and $CuSO_4$, and, optionally, one or more secondary carbon sources, as discussed above. In certain cases, the carbon source of a known culture medium may be replaced by glycerol (e.g. raw glycerol). Raw glycerol-containing culture media are exemplified below.

As will be described in greater detail below, the culture medium may be employed to culture cells that contain a recombinant nucleic acid for expressing a protein. Since, in certain embodiments, the recombinant nucleic acid may contain a selectable marker in order to select cells containing the recombinant nucleic acid, the culture medium may also contain a selection agent, e.g., an antibiotic such as ampicillin, tetracycline, kanamycin, hygromycin, bleomycin, chloroamphenicol, streptomycin or phleomycin or a herbicide, to which the selectable marker of the cells provides resistance. In certain cases, the culture medium may also contain protein secreted from the cells. As will be described in greater detail below, the protein may be endogenous to the cells, or non-endogenous to the cells.

In particular embodiments, the culture medium may be specifically formulated for culturing particular cells (e.g., host cells that contain a recombinant nucleic acid for producing a protein). As will be described in greater detail below, such host cells include, but are not limited to, certain bacterial and fungal host cells.

The glycerol (e.g., raw glycerol) present in a subject culture medium may be from any source. In particular embodiments, the glycerol (e.g., raw glycerol) present in a subject culture medium may be a by-product of biodiesel or soap production methods, i.e., as a by-product of the production of combustible alkyl esters by transesterification of vegetable and/or animal triglycerides, or as a by-product of the production of fatty acid salts by saponification of vegetable and/or animal triglycerides. Commercial sources of glycerol are available, for example from Novance (France), Reidel-de Haen (Germany), Sigma-Aldrich, and ADM.

The subject culture medium may be made using any convenient method. In one embodiment, all of the components of the culture medium, including the raw glycerol and water, may be combined and sterilized, e.g., autoclaved or filtered before use. In another embodiment, raw glycerol may be added to the other components of the growth medium prior to use. The medium may contain agar or another solidifying agent if the medium is a solid medium.

Cell Cultures

A cell culture comprising: a) a plurality of host cells and b) the above-described culture medium is provided. In certain embodiments, the cells may contain a recombinant nucleic acid for producing a protein.

In particular embodiments, a subject host cell may be a bacterial cell including gram positive and gram negative bacterial cells of the following species: *Bacillus* sp., including, but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*; *Streptomyces* sp., including, but not limited to: *S. lividans*, *S. carbophilus*, *S. rubigenosus*, and *S. helvaticus*; *Pantoea* sp., including *P. citrea*; *Gluconobacter* sp.; *Erwinia* sp.; and *E. coli*.

In other embodiments, the subject host cell may be a fungal cell of the following species: *Trichoderma* sp., (e.g., *Trichoderma reesei* (previously classified as *T. longibrachiatum* and currently also known as *Hypocrea jecorina*), *Trichoderma viride, Trichoderma koningii,* and *Trichoderma harzianum*)); *Penicillium* sp., *Humicola* sp. (e.g., *Humicola insolens* and *Humicola grisea*); *Chrysosporium* sp. (e.g., *C. lucknowense*), *Gliocladium* sp., *Aspergillus* sp. (e.g., *Aspergillus oryzae, Aspergillus niger, Aspergillus nidulans, Aspergillus kawachi, Aspergillus aculeatus, Aspergillus japonicus, Aspergillus sojae,* and *Aspergillus awamori*), *Fusarium* sp., *Mucor* sp., *Neurospora* sp., *Hypocrea* sp., or *Emericella* sp., among others.

Methods for culturing such cells, including suitable culture media components that may be used to culture those cells, are known.

As noted above, the cells of the cell culture may contain a recombinant nucleic acid for expressing a protein. In certain embodiments, the recombinant nucleic acid may comprise an expression cassette for expressing the protein, i.e., a promoter, a coding sequence (i.e., a polynucleotide encoding the protein), and a terminator, where the promoter, coding sequence and terminator are operably linked such that the coding sequence is transcribed to produce an RNA, and that RNA is translated to produce the protein. Each of the promoter, coding sequence and terminator may be, independently, endogenous (i.e., native) or non-endogenous to the host cell. Likewise, the protein may be endogenous (i.e., native) or non-endogenous to the host cell. In certain embodiments, the coding sequence may be codon optimized for expression of the protein in a particular host cell. Since codon usage tables listing the usage of each codon in many cells are known in the art (see, e.g., Nakamura et al, Nucl. Acids Res. 2000 28: 292) or readily derivable, such nucleic acids can be readily designed giving the amino acid sequence of a protein to be expressed.

The encoded protein may be an enzyme, a therapeutic protein, a reporter protein, a selectable marker, a food additive or a foodstuff or the like.

In one embodiment, the protein may be an enzyme such as a carbohydrase, such as an α-amylase, a β-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, subtilisin, thermolysin, an aspartic proteinase, or trypsin; a lipase or esterase, such as a triglyceridase, a phospholipase, a pregastric esterase, a phosphatase, a phytase, an amidase, an iminoacylase, a glutaminase, a lysozyme, or a penicillin acylase; an isomerase such as glucose isomerase; an oxidoreductases, e.g., an amino acid oxidase, a catalase, a chloroperoxidase, a glucose oxidase, a hydroxysteroid dehydrogenase or a peroxidase; a lyase such as a acetolactate decarboxylase, an aspartic β-decarboxylase, a fumarase or a histadase; a transferase such as cyclodextrin glycosyltranferase; or a ligase, for example. In particular embodiments, the protein may be an aminopeptidase, a carboxypeptidase, a chitinase, a cutinase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase, for example.

In other embodiments, the protein may be a therapeutic protein (i.e., a protein having a therapeutic biological activity). Examples of suitable therapeutic proteins include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Antibody proteins, (polypeptides comprising a framework region from an immunoglobulin gene or fragments thereof that specifically bind and recognize an antigen (e.g. monoclonal antibodies that may be humanized), are of particular interest.

In a further embodiment, the protein may be a reporter protein. Such reporter proteins may be optically detectable or colorigenic, for example. In this embodiment, the protein may be a β-galactosidase (lacZ), β-glucuronidase (GUS), luciferase, alkaline phosphatase, nopaline synthase (NOS), chloramphenicol acetyltransferase (CAT), horseradish peroxidase (HRP) or a fluorescent protein green, e.g., green fluorescent protein (GFP), or a derivative thereof.

Examples of selectable markers include but are not limited to ones that confer antimicrobial resistance (e.g. resistance to hygromycin, bleomycin, chloroamphenicol or phleomycin), and proteins that confer metabolic advantage, e.g., amdS, argB and pyr4. Selectable markers are further described in Kelley et al., (1985) EMBO J. 4: 475-479; Penttila et al., (1987) Gene 61:155-164 and Kinghorn et al (1992) Applied Molecular Genetics of Filamentous Fungi, Blackie Academic and Professional, Chapman and Hall, London.

In certain embodiments, the coding sequence may encode a fusion protein. In some of these embodiments, the fusion protein may provide for secretion of the protein from the host cell in which it is expressed and, as such, may contain a signal sequence operably linked to the N-terminus of the protein, where the signal sequence contains a sequence of amino acids that directs the protein to the secretory system of the host cell, resulting in secretion of the protein from the host cell into the medium in which the host cell is growing. The signal sequence is cleaved from the fusion protein prior to secretion of the protein. The signal sequence employed may be endogenous or non-endogenous to the host cell and, in certain embodiments, may be signal sequence of a protein that is known to be highly secreted from a host cell. In particular embodiments, the signal sequence protein may be any signal sequence that facilitates protein secretion from a filamentous fungal (e.g., *Trichoderma* or *Aspergillus*) host cell, or a bacterial (e.g., *Bacillus* or *Streptomyces*) host cell. Such signal sequences include, but are not limited to: the signal sequence of cellobiohydrolase I, cellobiohydrolase II, endoglucanases I, endoglucanases II, endoglucanases III, α-amylase, aspartyl proteases, glucoamylase, mannanase, glycosidase and barley endopeptidase B (see Saarelainen, Appl. Environ. Microbiol. 1997 63: 4938-4940), for example. Other of signal sequences are those originating from the fungal amyloglucosidase (AG) gene (glaA), the α factor gene (yeasts e.g. *Saccharomyces, Kluyveromyces* and *Hansenula*) or the α amylase gene (*Bacillus*). In certain embodiments, therefore, the subject recombinant nucleic acid may comprise: a signal sequence-encoding nucleic acid operably linked to a protein-encoding nucleic acid, where translation of the nucleic acid in a host cell produces a fusion protein comprising a protein having an N-terminal signal sequence for secretion of the protein from the host cell.

In particular embodiments, the fusion protein may further contain a "carrier protein", which is a portion of a protein that is endogenous to and highly secreted by the host cell. Suitable carrier proteins include those of *T. reesei* mannanase I (Man5A, or MANI), *T. reesei* cellobiohydrolase II (Cel6A, or CBHII) (see, e.g., Paloheimo et al Appl. Environ. Microbiol. 2003 December; 69 (12): 7073-7082) or *T. reesei* cellobiohydrolase I (CBHI). In one embodiment, the carrier protein is a truncated *T. reesei* CBH1 protein that includes the CBH1 core region and part of the CBH1 linker region. A fusion protein containing, from amino-terminus to carboxy-terminus, a signal sequence, a carrier protein and a subject protein in operable linkage is therefore provided, as well as a nucleic acid encoding the same.

A subject recombinant nucleic acid may be present in a vector, or integrated into the genome of a host cell. The recombinant nucleic acid may be present in a vector, e.g., a phage, plasmid, viral, or retroviral vector that autonomously replicates in the host cell. Vectors for expression of recombinant proteins are well known in the art (Ausubel, et al, Short Protocols in Molecular Biology, 3rd ed., Wiley & Sons, 1995; Sambrook, et al., Molecular Cloning: A Laboratory Manual, Second Edition, (1989) Cold Spring Harbor, N.Y.).

Since the culture media described above contains raw glycerol, which, in certain embodiments may be the glycerol-containing by-product of the reactions used to make biodiesel or soap, the culture media may in certain embodiments contain trace, detectable amounts, e.g., less than 1%, less than 0.5%, less than 0.2%, less than 0.1%, less than 0.05%, less than 0.01%, less than 0.005%, less than 0.001%, or less than 0.0005% (v/v) of components used in, or other products or by-products of, those reactions. For example, in certain embodiments, a subject culture medium may contain trace amounts of alkyl esters or alkyl salts of the fatty acids found in the triglycerides of plant oils, e.g., the oils of rapeseed, soybean, thiol mustard, palm, hemp, jatropha, waste cooking oil or animal fats, e.g., tallow, lard, yellow grease or fish oil, soap, a reaction catalyst, e.g., sodium methoxide or sodium silicate, or an alcohol, e.g., ethanol or methanol, fatty acid, ash, sulfates, phosphates, acetates and e-methoxy, 1,2-propanediol, depending on the reaction employed to produce the raw glycerol.

Methods

The above-described cell culture may be made using a variety of different methods. For example, in certain embodiments, a culture medium containing raw glycerol may be made, e.g., by mixing all the components of the culture medium together in water, adding raw glycerol, and then inoculating the culture medium with host cells. The cell culture may be maintained under suitable conditions for growth of the cells in a vessel (e.g., in a shaking incubator at a suitable temperature, such as room temperature, 30° C. or 37° C. in bioreactors).

In other embodiments, the raw glycerol may be added to (e.g., mixed with) a culture of cells. In these embodiments, the raw glycerol may be combined with the cell culture rapidly, e.g., over a few seconds, or gradually, e.g., over a few minutes or hours. As such, in certain embodiments, the subject methods may include culturing cells in the absence of raw glycerol (i.e., using a carbon source that is not raw glycerol), and then adding the raw glycerol to the cells. In other embodiments, the cells are cultured in the presence of the raw glycerol for a period of time (e.g., minutes or hours) and then another carbon source is added to the culture. As noted above, the raw glycerol may or may not be a sole carbon source for the cells of the cell culture.

In particular embodiments, the raw glycerol may be received from a remote location, e.g., a soap or biodiesel manufacturing facility that is at a location that is remote to the location of the cell culture, e.g., a different city or state, prior to use. The raw glycerol may be stored, and sterilized prior to use.

Methods of using the above-described cell culture to produce a protein are also provided. In certain embodiments, the subject protein production methods include: maintaining the above-described cell culture to provide for production of the protein. In certain embodiments and as discussed above, the protein may be secreted into the culture medium. As such, certain embodiments of the method include the step of recovering the protein from the culture medium. The protein produced by the cells may be employed in a variety of methods.

In some embodiments, a cell may be cultured under batch or continuous fermentation conditions. Classical batch fermentation methods use a closed system, where the culture medium is sterilized prior to the beginning of the fermentation run, the medium is inoculated with the desired organism(s), and fermentation occurs without the subsequent addition of any components to the medium. In certain cases, the pH and oxygen content, but not the carbon source content, of the growth medium may be altered during batch methods. The metabolites and cell biomass of the batch system change constantly up to the time the fermentation is stopped. In a batch system, cells usually progress through a static lag phase to a high growth log phase and finally to a stationary phase where growth rate is diminished or halted. If untreated, cells in the stationary phase eventually die. In general terms, the cells in log and stationary phases produce most protein.

A variation on the standard batch system is the "fed-batch fermentation" system. In this system, nutrients (e.g., a carbon source such as raw glycerol, nitrogen source, salts, $O_2$, or other nutrient) are added when their concentration in culture falls below a threshold. Fed-batch systems are useful when catabolite repression is apt to inhibit the metabolism of the cells and where it is desirable to have limited amounts of nutrients in the medium. Measurement of the actual nutrient concentration in fed-batch systems is estimated on the basis of the changes of measurable factors such as pH, dissolved oxygen and the partial pressure of waste gases such as $CO_2$. Batch and fed-batch fermentations are common and known in the art.

Continuous fermentation is an open system where a defined culture medium containing raw glycerol is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source (raw glycerol) or nitrogen source is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off may be balanced against the cell growth rate in the fermentation. Methods of modulating nutrients and growth factors for continuous fermentation processes as well as techniques for maximizing the rate of product formation are known.

The fermentation reaction is an aerobic process in which molecular oxygen may be supplied by for example molecular oxygen containing gas such as air or oxygen enriched air. Although aeration rate may vary over a considerable range, aeration is generally conducted as a rate which is in the range of about 0.5 to 10, preferably about 0.5 to 7, volumes (at the pressure employed at 25° C.) of oxygen-containing gas per liquid volume in the fermentor per minute. This amount is based on air of normal oxygen content being supplied to the reactor, and in terms of pure oxygen the respective range would be about 0.1 to 1.7 volumes (at the pressure employed and at 25° C.) of oxygen per liquid volume in the fermentor per minute. The pressure range employed for the microbial conversion process can vary widely. Pressures generally are within the range of about 0 to 50 psi.

The fermentation temperature can vary somewhat, but for filamentous fungi and bacteria the temperature will generally be within the range of 20° C. to 45° C. depending on the strain and organism.

The source of nitrogen which is required by the microorganisms may be any nitrogen containing compound or compounds capable of releasing nitrogen in a form suitable for metabolic utilization by the microorganism. While a variety of organic nitrogen sources compounds such as protein hydrolysates can be used, usually inexpensive nitrogen containing compounds such as ammonia, ammonium hydroxide, urea ammonium sulfate, ammonium phosphate, ammonium chloride and other ammonium compounds are utilized. Ammonium gas may be used for large scale operations and can be employed by bubbling through the aqueous fermentation medium.

The pH range in an aqueous microbial fermentation should be in the exemplarily range of pH 2.0 to 8.0. For some microorganisms the pH will be in the range of pH 3.5 to 6.0 and for other microorganisms the preferred pH will be pH 6.0 to 7.5. While the average fermentation time will vary greatly depending on the type of culture or fermentation that is contemplated, in general the run time will be between 12 and 400 hours.

The type of fermentor employed is not critical, though for example a 15 L Biolafitte (Saint-Germain-en-Laye-, France) may be used. In some embodiments, the fermentation broth will generally contain cellular debris, including cells and various suspended solids and potentially other biomass containments as well as the desired protein. Protein may be recovered from growth media by any convenient method, e.g., by precipitation, centrifugation, affinity, filtration or any other method known in the art.

In some embodiments, the fermentation will include an inducing feed composition for stimulating the expression of desired proteins in certain host cells. For example, when Trichoderma is the host cell and particularly when Trichoderma is used as a host cell for the production of cellulase genes, an inducing feed composition may be utilized and reference is made to WO 04/035070 published Apr. 29, 2004.

In some embodiments, the use of raw glycerol-containing culture medium provides a greater amount of cell mass and/or secreted protein than other culture media that solely contain a sugar-based carbon source. For example, in certain embodiments cells cultured in culture medium containing raw glycerol may produce at least 2% more protein, at least 5% more protein, at least 10% more protein, at least 50% more protein, at least 100% more protein or at least 1000% more protein than an equivalent culture containing a sugar-based carbon source (e.g., sucrose or glucose), i.e., a cell culture containing the same cells, cultured in an equivalent sugar-containing medium under the same conditions for the same amount of time. More specifically a cell culture comprising raw glycerol as the sole carbon source may produce at least 5% more protein than an equivalent culture comprising a 6-carbon sugar (e.g. glucose) or a mixture of 6 carbon sugars (e.g. sucrose, glucose, fructose) as the sole carbon source. In some embodiments, the cell mass will be the same or greater for cells grown in a medium containing raw glycerol as compared to equivalent cells grown in a sugar based carbon source (e.g. glucose or sucrose without glycerol). For example the cell mass as measured by grams of cells/kg may be 1%, 2%, 3% 5% 10%, 20% or greater for cells grown with a glycerol feed as compared to a glucose feed when measured at the same time period (e.g. at 20, 30 or 40 hours).

EXAMPLES

In order to further illustrate the present invention and advantages thereof, the following specific examples are given with the understanding that they are being offered to illustrate the present invention and should not be construed in any way as limiting its scope.

Materials and methods suitable for the maintenance and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg, and G. Briggs Phillips, eds.), American Society for Microbiology, Washington, D.C. (1994) or Thomas D. Brock in *Biotechnology: A Textbook of Industrial Microbiology*, Second Edition (1989) Sinauer Associates, Inc., Sunderland, Mass. All reagents and materials used for growth and maintenance of bacterial cells were obtained from Sigma Aldrich (St. Louis, Mo.), GD (Franklin Lakes, N.J.), or QBiogene (Irvine, Calif.) unless otherwise specified.

In the disclosure and experimental section which follows, the following abbreviations apply: ° C. (degrees Centigrade); rpm (revolutions per minute); $H_2O$ (water); $dH_2O$ (deionized water); $dIH_2O$ (deionized water, Milli-Q filtration); aa or AA (amino acid); by (base pair); kb (kilobase pair); kD (kilodaltons); g or gm (grams); µg (micrograms); mg (milligrams); µL (microliters); ml and mL (milliliters); mm (millimeters); µm (micrometer); M (molar); mM (millimolar); µM (micromolar); V (volts); MW (molecular weight); sec(s) or s(s) (second/seconds); min(s) or m(s) (minute/minutes); hr(s) or h(s) (hour/hours); DIFCO (DIFCO Laboratories); m/v (mass/volume); and v/v (volume/volume); OUR (amount of oxygen used for respiration by microorganisms per unit fermentor volume over unit time); DO % (amount of oxygen dissolved in fermentation broth relative to maximum soluble amount as measured by membrane probe).

Sources of raw glycerol used in the examples below are provided in Table 1.

TABLE 1

| Type | Glycerol (%) | Salt (%) | M.O.N.G. (%) |
|------|--------------|----------|--------------|
| 1 | 78.0-82.0 | 6.0-7.0 | <0.50 |
| 2 | 94.6 (desalted) | 0 | 0.13 |
| 3 | 80.0 | 5.0 | N.A. |
| 4 | 88.0-93.0 | N.A. | 0.25 |
| 5 | 98.0 | N.A. | 1.20 |

M.O.N.G.—Matter Organic Non Glycerol
N.A.—information not available

Example 1

*Streptomyces lividans* Grown in Batch Culture

*Streptomyces lividans* cells expressing a neutral cellulase from *Cellulomonas* were cultivated under aerobic submerged conditions by conventional batch fermentation in 500 mL shake flasks with 50 mL working volume. The nutrient medium contained yeast extract (Biospringer B), ammonium sulfate, citric acid, and magnesium sulfate, in solid form and a solution of boric acid, citric acid, ferrous sulfate, manganese chloride, zinc sulfate, and either 1% (w/v) glucose or raw glycerol.

Specific reference is made to U.S. Pat. No. 7,135,309 in Example 16 and PCT Application No. WO 06/071598A1 in Example 2 for a detailed description of a culture and production medium which was used for cell cultures. In brief, cultures in rich media shake-flasks are started by inoculation from two-days old TSA-plates (trypticase soy agar, BBL #11043). Other rich media are either TSB (trypticase soy broth; BBL #11768), Liquid Broth (which contains per liter: 16 g tryptone, 10 g yeast extract, and 5 g NaCl), medium B (TSB supplemented with per L: 10.0 g glycerol, 2 mL Modified Balch's Trace-Element Solution in which NTA is replaced by citric acid, The composition of Modified Balch's Trace-Element Solution can be found in Methods for General and Molecular Bacteriology (P. Gerhardt et al., eds, p. 158, American Society for Microbiology, Washington, D.C. (1994)). Cultures in minimal media shake-flasks are started by inoculation from two-days old liquid TSB cultures, using a 1/30 (v/v) inoculum. Minimal media are either: MM322 (which contains per liter: 12.0 g glycerol, 11.3 g $K_2HPO_4$, 1.0 g $(NH_4)_2SO_4$, 0.2 g Difco yeast extract, 0.1 g NaCl, and 10 mL Modified Balch's Trace-Element Solution modified as above, final pH 6.7 (HCl)); medium D (medium MM322 supplemented with 2 g Na2CO3/L final pH 7.2); or medium E (Medium Dm, final pH 6.4). Media B and C and the minimal media are filter-sterilized, the other media are autoclaved.

In addition, suitable culture conditions may be found in the scientific literature, such as Sambrook (1989), supra; Kieser et al. (2000) *Practical Streptomyces Genetics*, John Innes Foundation, Norwich, UK; and from the American Type Culture Collection (ATCC), www.atcc.org.

Figure 2:
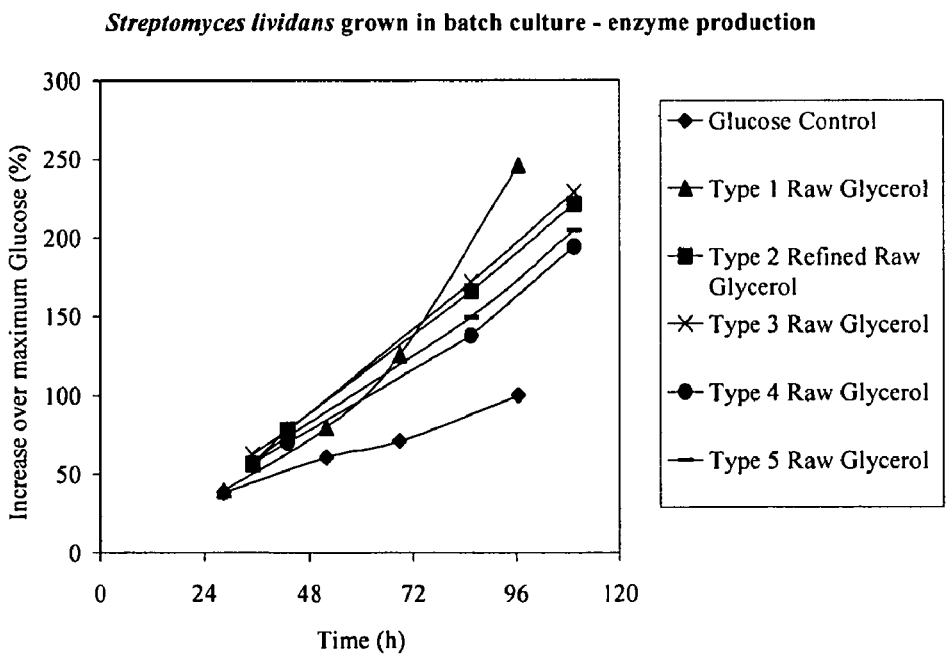
FIG. 2 depicts the amount of cellulase secreted by *Streptomyces lividans* grown in batch culture over time, cultured in media containing raw glycerol or glucose (% increase over maximum glucose), as described in Example 1. All data points are depicted as relative to the highest level of protein produced in the medium with glucose, which is set at 100%.

The shake flasks were incubated at 30° C. and shaken vigorously. Samples were taken over the time course of 5 days and cell growth (DCW) and protein production were analyzed by assaying cellulase activity. DCW was measured using the OMNIMARK µWave (Omnimark Instruments Corporation, Tempe, Ariz.). Cellulase activity was determined according to standard techniques (see the microtiter plate assay described in PCT Application Nos. PCT/US2005/045859 and WO 06/071598). The results are presented in FIGS. 1 and 2.

Example 2

*Streptomyces lividans* Grown in Fed-Batch Culture

Figure 3:
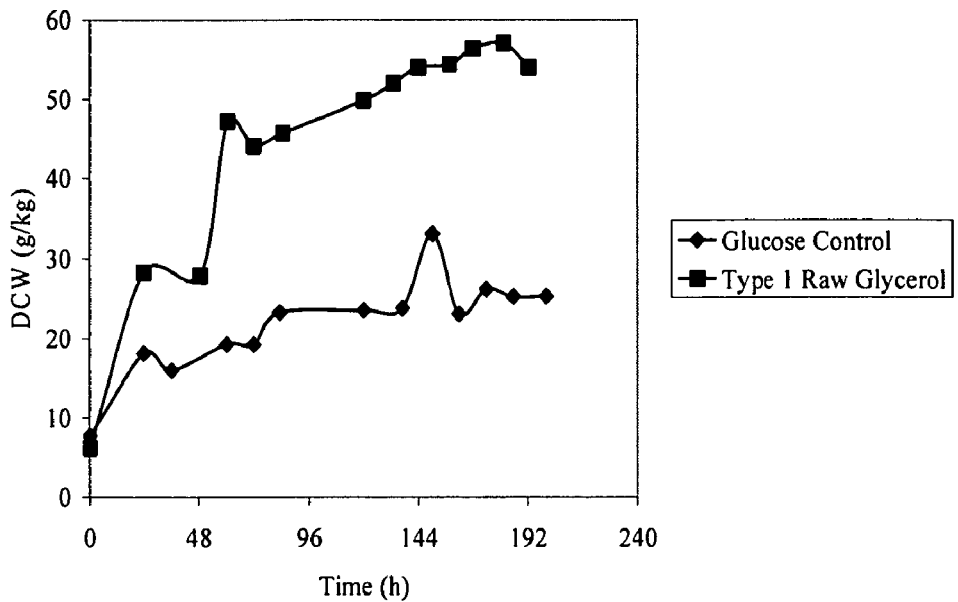
FIG. 3 depicts the cell mass of recombinant *Streptomyces lividans* cells grown in fed-batch culture over time (DCW; grams of cells/kg), cultured in media containing raw glycerol or glucose, as described in Example 2.
Figure 4:
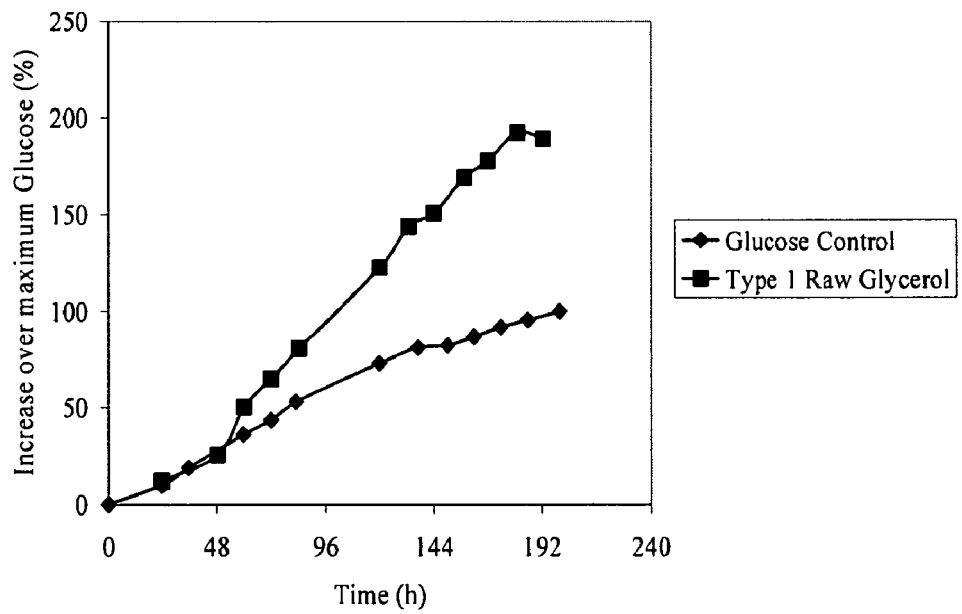
FIG. 4 depicts the amount of cellulase secreted by *Streptomyces lividans* grown in fed-batch culture over time, cultured in media containing raw glycerol or glucose (% increase over maximum glucose), as described in Example 2. All data points are depicted as relative to the highest level of protein produced in the medium with glucose, which is set at 100%.

*Streptomyces lividans* expressing a neutral cellulase from *Cellulomonas* was cultivated under aerobic submerged conditions by conventional fed-batch fermentation in a nutrient medium which is described above in Example 1. 14 L batch fermentations were fed with a 60% wt/wt glucose feed (Cargill DE99 dextrose) or the equivalent 60% wt/wt raw glycerol. Feed was started at 20 oxygen uptake rate (OUR in mmol/L-h). The feed rate was ramped over several hours. The feed rate was adjusted on an equal carbon basis for glycerol feeding. The pH was controlled at pH 7.0 using 28% w/v ammonium hydroxide. The fermentation temperature was controlled at 32° C. and agitated vigorously. Various other parameters such as pH, DO %, airflow, and pressure were monitored throughout the entire process. The DO % was maintained above 30. Samples were taken over the time course of 5 days and analyzed for cell growth (DCW) and protein production. The graphs of FIGS. 3 and 4 show the results of these experiments.

Example 3

*Bacillus subtilis* Grown in Batch Culture

Cells of the microorganism *Bacillus subtilis* expressing a *B. amyloliquefaciens* serine protease were cultivated under aerobic submerged conditions by conventional batch fermentation in 500 mL shake flasks with 50 mL working volume. The nutrient medium contained 7 g/l soy meal (Cargill), 0.03 g/l magnesium sulfate, 0.22 g/l potassium phosphate dibasic, 21 g/l sodium phosphate monobasic and 16 g/l dibasic in solid form and a solution of 3.6 g/l urea, glucose or raw glycerol at 5%. The pH after autoclaving was 7.5. Glucose or glycerol was added after sterilizing the soy meal and salt medium including urea. Other medium recipes include those described in Arbige et al., Fermentation of *Bacillus*, pgs 871-891 and Ferrari et al., Commercial Production of Extracellular Enzymes, pgs 917-937, both in Sonenshein et al., *Bacillus subtilis* and Other Gram-positive Bacteria: Biochemistry, Physiology and Molecular Genetics, (1993) American Society for Microbiology. Specific reference is made to U.S. Pat. No. 7,135,309 in Example 17 for a description of the culture and production media which may be used.

Figure 5:
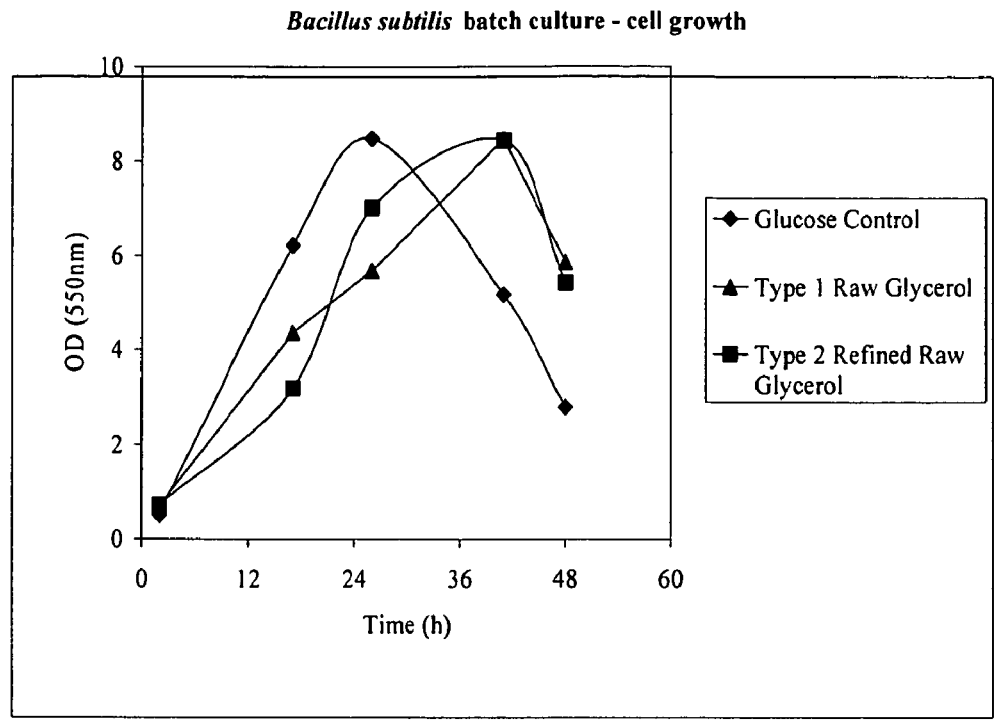
FIG. 5 depicts the cell mass of recombinant *Bacillus subtilis* cells grown in batch culture over time (optical density at 550 nm), cultured in media containing raw glycerol or glucose, as described in Example 3.
Figure 6:
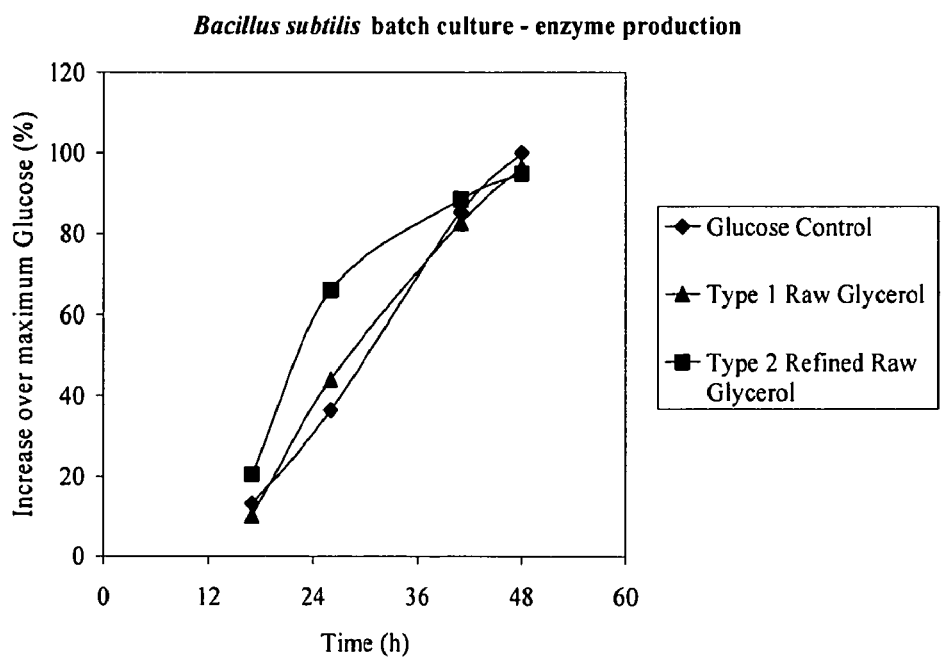
FIG. 6 depicts the amount of protease secreted by *Bacillus subtilis* grown in batch culture over time, cultured in media containing raw glycerol or glucose (% increase over maximum glucose), as described in Example 3. All data points are depicted as relative to the highest level of protein produced in the medium with glucose, which is set at 100%.

The shake flask was placed at 37° C. and shaken at 170 rpm (2" shaker throw). Samples were taken over the time course of 2 days and analyzed for cell growth (optical density at 550 nm; "OD550") and protein production. Optical density was measured using the Spectronic Genesys 2 at 550 nm (Sprectronic Analytical Instruments, Garforth, West Yorkshire, UK). Optical density (OD) may also be measured by techniques that are well known in the art, for example, as described in *Manual of Methods for General Bacteriology* (Phillipp Gerhardt, R. G. E. Murray, Ralph N. Costilow, Eugene W. Nester, Willis A. Wood, Noel R. Krieg, and G. Briggs Phillips, eds.). Protein production also determined as described in Estell et al. (1985) *J. Biol. Chem.* 260 (11):6518-21. The graphs of FIGS. 5 and 6 shown the results of this experiment.

Example 4

*Bacillus subtilis* Grown in Fed-Batch Culture

Figure 7:
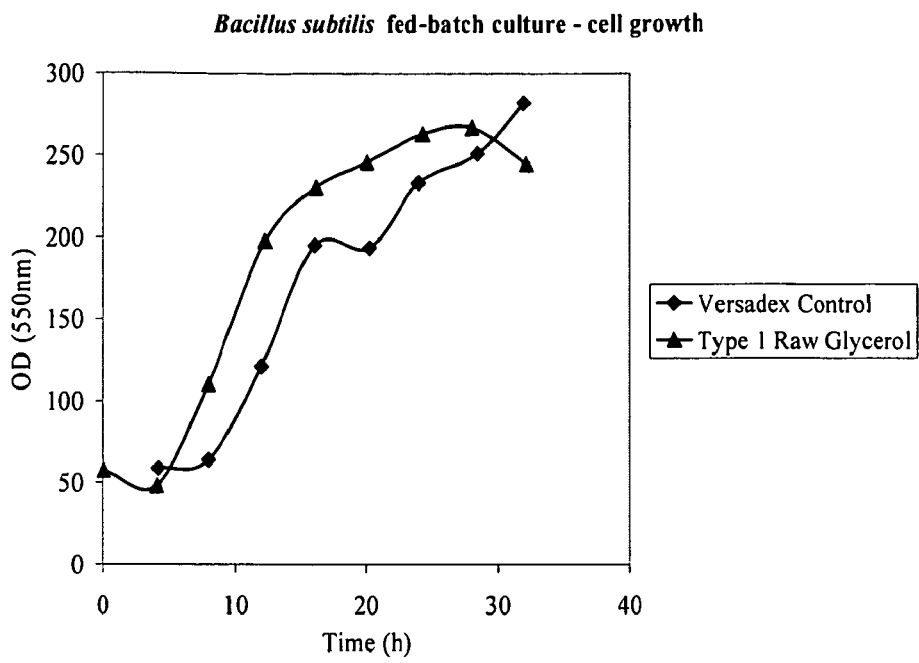
FIG. 7 depicts the cell mass of recombinant *Bacillus subtilis* cells grown in fed-batch culture over time (optical density at 550 nm), cultured in media containing raw glycerol or glucose, as described in Example 4.
Figure 8:
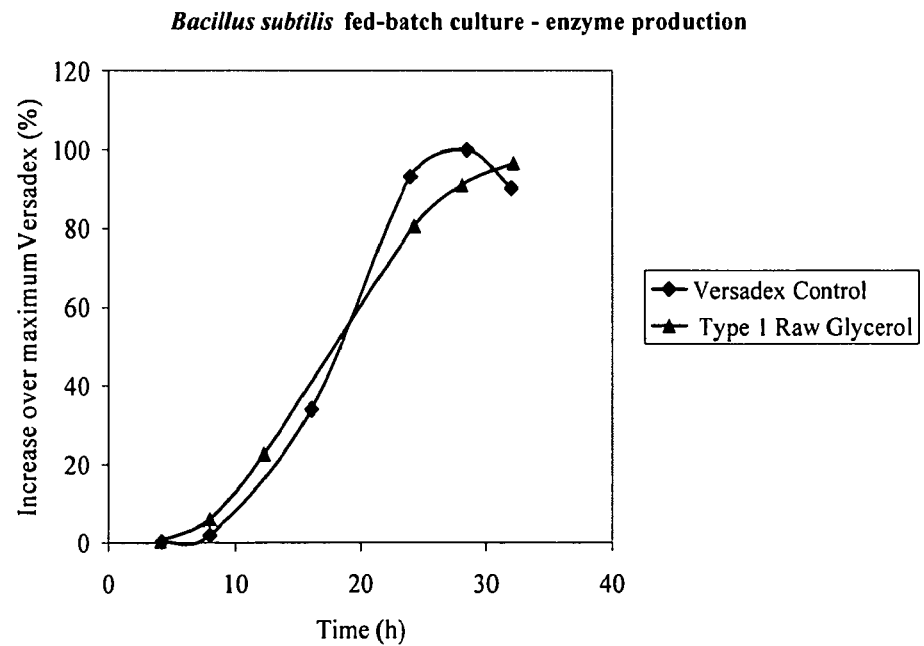
FIG. 8 depicts the amount of protease secreted by *Bacillus subtilis* grown in fed-batch culture over time, cultured in media containing raw glycerol or glucose (versadex) (% increase over maximum versadex), as described in Example 4. All data points are depicted as relative to the highest level of protein produced in the medium with versadex, which is set at 100%.

The microorganism *Bacillus subtilis*, expressing a *B. amyloliquefaciens* serine protease was cultivated under aerobic submerged conditions by conventional fed-batch fermentation essentially as described by K. Anstrup (1974) *Industrial Aspects of Biochemistry*, B. Spencer, ed., pp. 23-46, in a nutrient medium containing 0-15% soy meal (Cargill), 5-25 g/l sodium and potassium phosphate, 0.5-4 g/l magnesium sulfate and a solution of 5-15 g/l citric acid, ferric chloride and manganese chloride. Prior to fermentation the media was macerated for 90 minutes using a mixture of enzymes including cellulases, hemicellulases and pectinases (see, WO95/04134). 14 L batch fermentations were fed with 60% wt/wt glucose feed (Cargill DE99 dextrose), versadex greens or invert sugar or the equivalent 60% wt/wt raw glycerol (Biodiesel By-Product). Feed was started when glucose or glycerol in batch were non-detectable. The feed rate was ramped over several hours. The feed rate was adjusted to add raw glycerol on an equal carbon basis. The pH was controlled at 7 using 28% w/v ammonium hydroxide. In case of foaming antifoam agent was added to the media (Mazu DF 204, 1-3 g/L). The fermentation temperature was controlled at 37° C. and agitated at 750 rpm. Various other parameters such as pH, DO %, airflow, and pressure were monitored throughout the entire process. The DO % was maintained above 20. Samples were taken over the time course of 2 days and analyzed for cell growth (OD550 nm) and protein production. Cell growth and protein production were measured as described in Example 3. The graphs of FIGS. 7 and 8 show the results of these experiments.

Example 5

T. reesei Grown in Batch Culture

Trichoderma reesei cells expressing a Trichoderma glucoamylase are cultivated by batch fermentation in shake flask. Transformants were maintained on Vogel's minimal medium (Davis et al., (1970) Methods in Enzymology 17A, pg 79-143 and Davis, Rowland, Neurospora, Contributions of a Model Organism, Oxford University Press (2000)). Baffled shake flasks with 50 mL of either lactose or Proflo medium are inoculated with agar blocks of fungal culture. The shake flask is incubated at 30° C. and shaken at 170 rpm (2" shaker throw). Samples are taken over the time course of 4 days and analyzed for cell growth (dry cell weight) and enzyme activity. The dry cell weight (DCW) is determined according to the standard method by measuring the weight before and after the drying process in g/kg (MVIMARK Instrument Corporation µWave).

The lactose medium consists of: 10 g/L lactose; 2 g/L peptone; 1 g/L yeast extract; 15 g/L $KH_2PO_4$; 2 g/L $(NH_4)_2SO_4$; 0.3 g/L $MgSO_4*7H_2O$; 0.3 g/L $CaCl_2*2H_2O$; 1 mL/L trace metal stock solution.

Proflo medium is composed of: 22.5 g/L Proflo; 30 g/L lactose; 6.5 g/L $(NH_4)_2SO_4$; 2 g/L $KH_2PO_4$; 0.3 g/L $MgSO_4*7H_2O$; 0.2 g/L $CaCl_2$; 0.72 g/L $CaCO_3$; 1 mL/L trace metal stock solution and 2 mL/L of 10% Tween 80.

The T. reesei trace metal stock solution used in both media has 5 g/L $FeSO_4*7H_2O$; $MnSO_4*H_2O$ 1.6; 1.4 g/L $ZnSO_4*7H_2O$; 2.8 g/L $CoCl_2*6H_2O$.

In both media the pH is adjusted to 5.5 using 28% w/v ammonium hydroxide or 5N HCl. Glucose or raw glycerol are added at 1.5% of the final concentration to either media as additional carbon source supporting growth.

Example 6

A. niger Grown in Batch Culture

Cells of the fungus Aspergillus niger expressing an Aspergillus glucoamylase were cultivated under aerobic submerged conditions by conventional batch fermentation in shake flasks containing 50 mL of A. niger in a suitable nutrient medium for 5 days. The medium contained a carbon source, for example, maltose or raw glycerol, a nitrogen source, and inorganic salts, using procedures known in the art. Suitable media are available from commercial suppliers or may be prepared according to published compositions, e.g., in catalogues of the American Type Culture Collection or as described in Ward et al. Bio/Technology 8:435-440 (1990), in U.S. Pat. No. 5,360,732, or in U.S. Pat. No. 7,135,309B1 in Examples 22 and 23.

Figure 9:
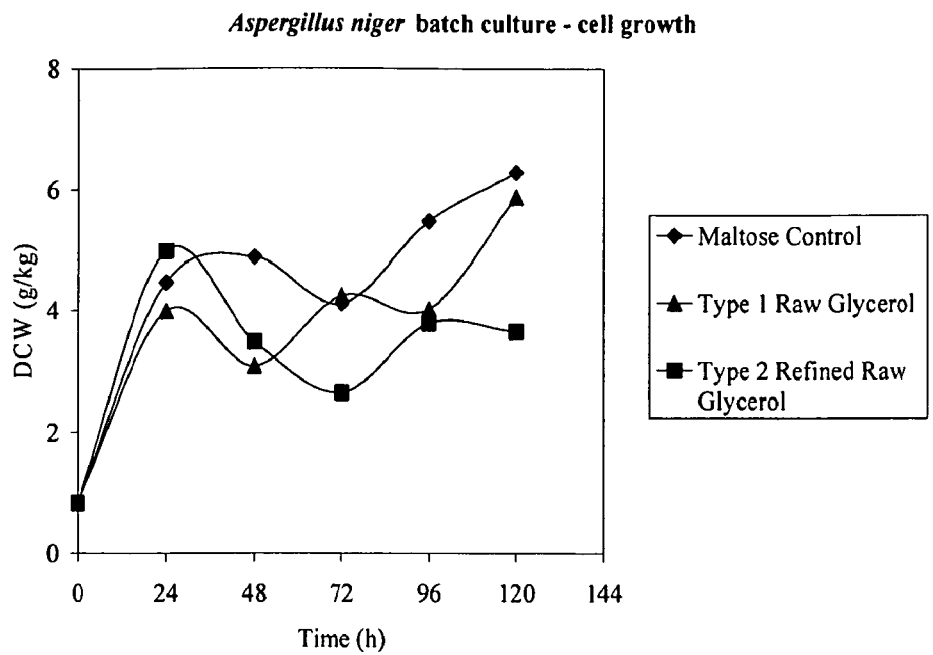
FIG. 9 depicts the cell mass of non-recombinant *Aspergillus niger* cells grown in batch culture over time (DCW; grams of cells/kg), cultured in media containing raw glycerol or maltose, as described in Example 6.
Figure 10:
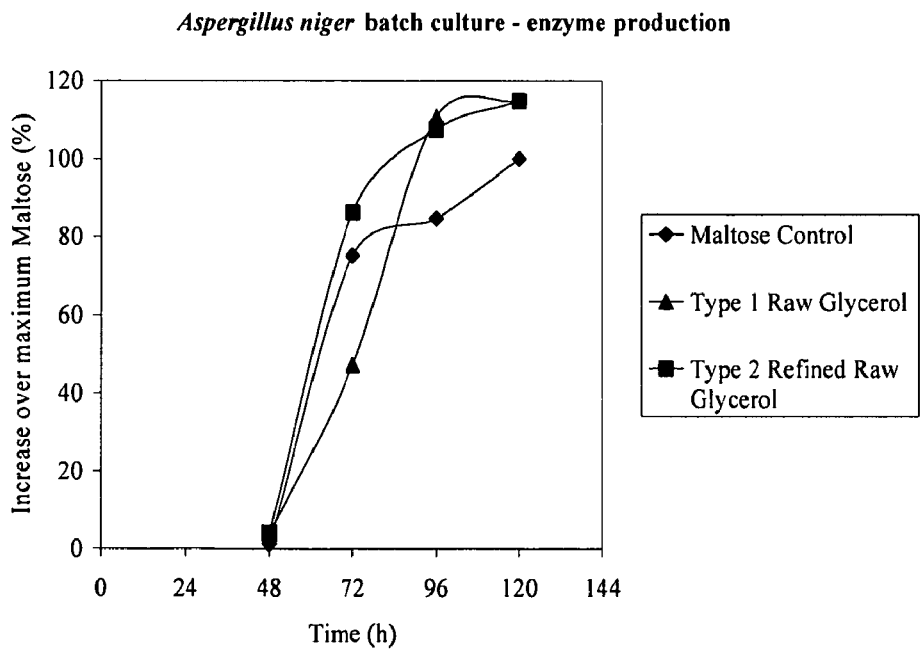
FIG. 10 depicts the amount of glucoamylasae secreted by *Aspergillus niger* grown in batch culture over time, cultured in media containing raw glycerol or maltose (% increase maximum maltose), as described in Example 6. All data points are depicted as relative to the highest level of protein produced in the medium with maltose, which is set at 100%.

The nutrient medium used in this study contained promosoy 100 (full-fat soy concentrate, Central Soya Co., Chicago, Ill.; see U.S. Pat. No. 3,971,856) and ammonium sulfate, magnesium sulfate anhydrous, (tri) sodium citrate, sodium phosphate, as described in Ward et al. (2004) Appl. Environ. Microbiol. 70 (5):2567-76 and 5% (w/v) maltose or raw glycerol as an equal replacement. The pH was adjusted to 4.8 with 5 N HCl. The medium was buffered at pH 4.5 with sodium phosphate. 1-3 g/l Mazu DF60-P (Mazur Chemicals, Inc., Gurnee, Ill.) was used as antifoam. The cells were grown for 5 days at 30° C. at 170 rpm (2" shaker throw) with vigorous agitation. Samples were taken over the time course of 5 days and analyzed for cell growth (DCW) and glucoamylase production by standard assays (see Ward et al. (2004) Appl. Environ. Microbiol. 70 (5):2567-76). The results are presented in FIGS. 9 and 10.

Example 7

Streptomyces rubiginosis Grown in Batch Culture

Streptomyces rubiginosis cells expressing a Streptomyces rubiginosis glucose isomerase were cultivated under aerobic submerged conditions by conventional batch fermentation in 500 mL shake flasks with a 50 mL working volume. The flasks were started with 10% inoculum from a 24 h seed flask and cultured in a suitable nutrient media for 5 days. The nutrient media contained 4 g/l yeast extract (BD), 2.2 g/l Cerelose, 6 g/l potato dextrose starch, 0.5 g/l technical agar and 3.5 g/l ammonium sulphate and either 1.4% (w/v) glucose or raw glycerol was added to the flask. The pH was adjusted to 6 with 5 N HCl.

In addition, suitable culture conditions may be found in the scientific literature such as Sambrook, (1982) supra; T. Kieser, M J. Bibb, M J. Buttner, K F Chater, and D. A. Hopwood, et al., (2000) PRACTICAL STREPTOMYCES GENETICS. John Innes Foundation, Norwich UK; and/or from the American Type Culture Collection (ATCC; www.atcc.org).

Figure 11:
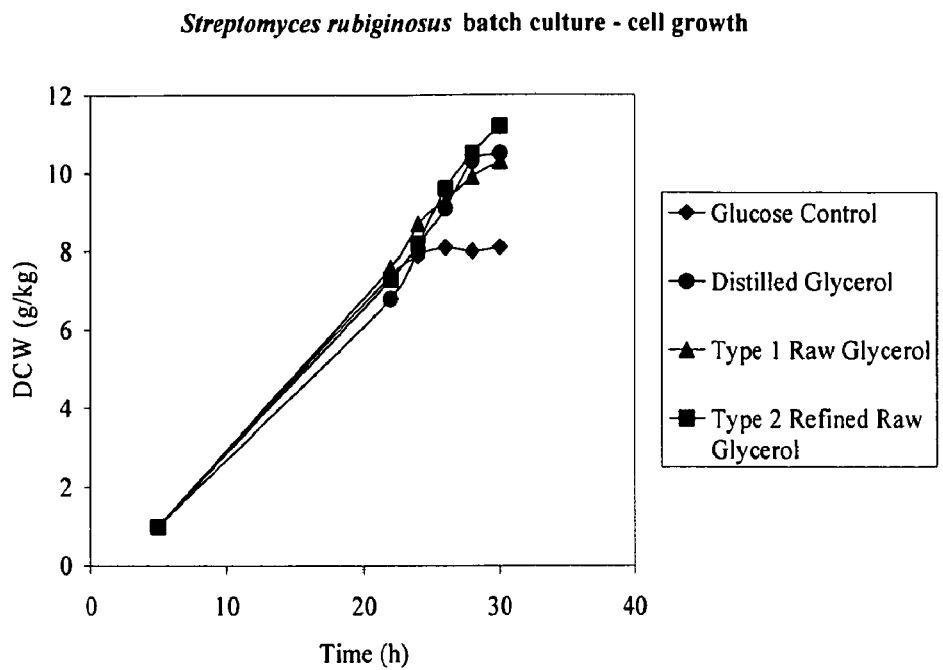
FIG. 11 depicts the cell mass of recombinant *Streptomyces rubigenosis* cells grown in batch culture over time (DCW; grams of cells/kg), cultured in media containing raw glycerol or glucose, as described in Example 7.
Figure 12:
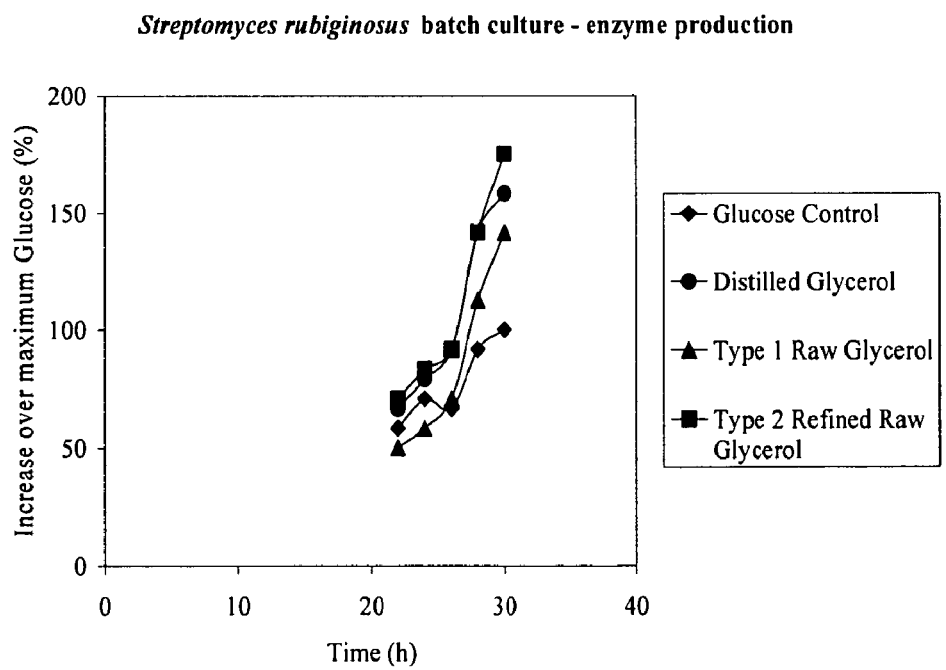
FIG. 12 depicts the amount of intracellular glucose isomerase secreted by *Streptomyces rubigenosis* grown in batch culture over time, cultured in media containing raw glycerol or glucose (% increase over maximum glucose), as described in Example 7. All data points are depicted as relative to the highest level of protein produced in the medium with glucose, which is set at 100%.

The shake flasks were incubated at 30° C. and vigorously agitated. 1 drop per liter Mazu DF60-P (Mazur Chemicals, Inc., Gurnee, Ill.) was used as antifoam. Samples were taken over the time course of 30 hours and cell growth (DCW) and protein production were analyzed by assaying glucose isomerase activity. Glucose isomerase activity was determined according to standard techniques (U.S. Pat. Nos. 4,610,965, 5,384,257, 5,310,665). The results are presented in FIGS. 11 and 12.

Example 8

Hansenula polymorpha Grown in Batch Culture

Figure 13:
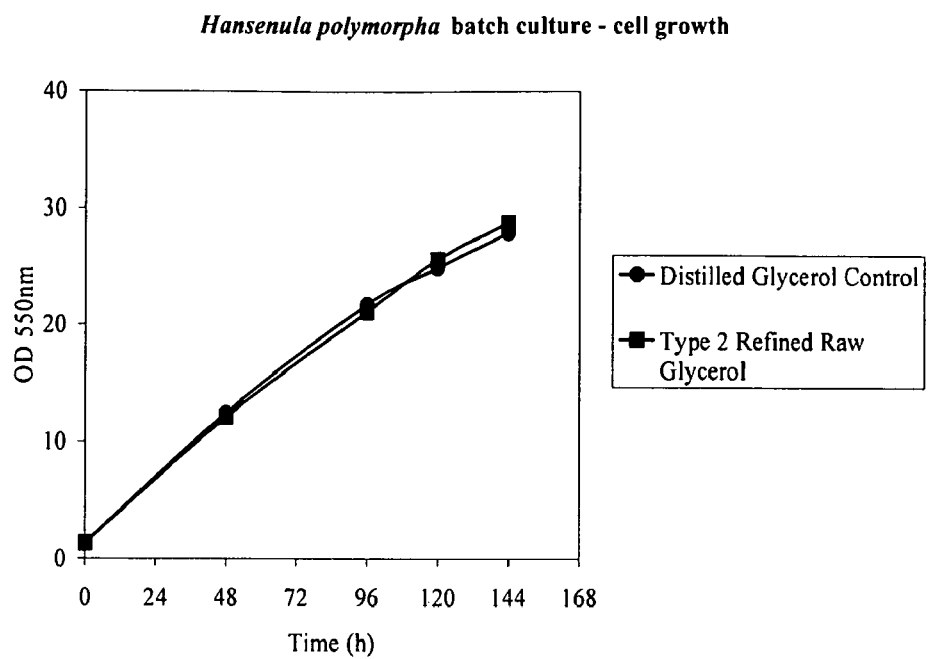
FIG. 13 depicts the cell mass of recombinant *Hansenula polymorpha* cells grown in batch culture over time (optical density at 550 nm), cultured in media containing distilled or raw glycerol, as described in Example 8.
Figure 14:
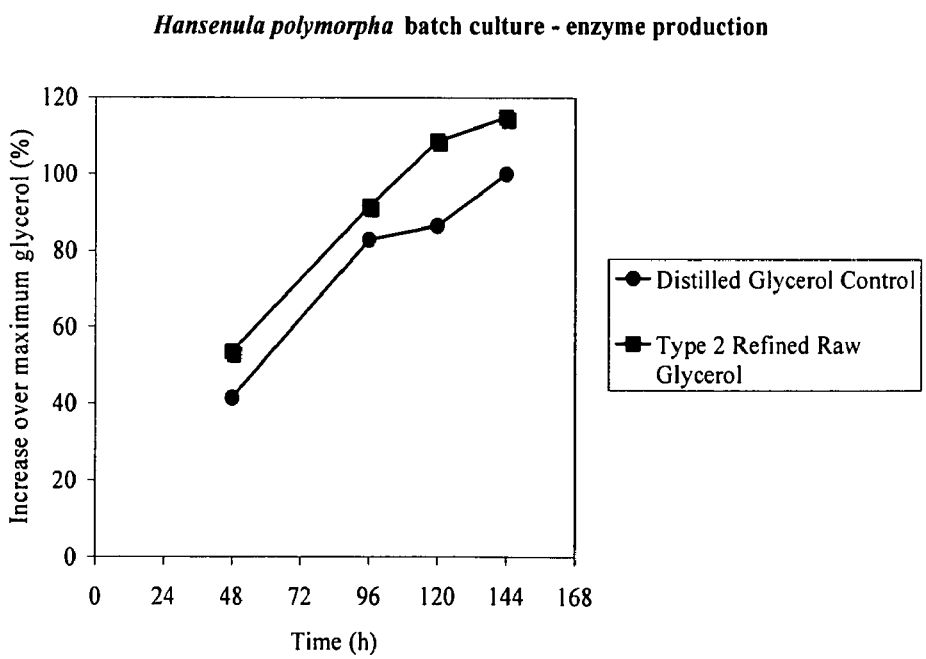
FIG. 14 depicts the amount of lipase secreted by *Hansenula polymorpha* grown in batch culture over time, cultured in media containing distilled or raw glycerol (% increase over maximum glycerol), as described in Example 8. All data points are depicted as relative to the highest level of protein produced in the medium with distilled glycerol, which is set at 100%.

Hansenula polymorpha expressing a recombinant fungal lipase (PCT Application No. WO 2005/087918) was grown in aerobic submerged conditions by conventional batch fermentation in YPD media (DIFCO). Cells were cultivated in 2.8 liter baffled fernbach shake flask with 0.75 liter working volumes. The media was adjusted to pH 6.1 with NaOH or $H_2SO_4$. The cultures were incubated at 26° C. and vigorously shaken at 170 rpm (2" shaker throw). One drop per liter Mazu DF204 was added to control foaming. Samples were taken over a time course of 6 days and cell growth (OD550 nm) and protein production were analyzed. Lipase activity was determined according to the "TIPU assay" (PCT Application No. WO 2005/087918). The results are presented in FIGS. 13 and 14.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for producing a protein in a host cell, comprising culturing said host cell in a culture medium that comprises raw glycerol at a concentration of 30% to 80% (v/v) as a carbon source, wherein said host cell comprises a recombinant nucleic acid that encodes said protein.

2. A method according to claim 1, wherein the culture medium further comprises a carbohydrate as a carbon source in addition to said raw glycerol.

3. A method according to claim 1, wherein said host cell is a bacterial cell.

4. A method according to claim 3, wherein said bacterial cell is selected from *Streptomyces lividans, Bacillus subtilis*, and *Streptomyces rubiginosis*.

5. A method according to claim 1, wherein said host cell is a fungal cell.

6. A method according to claim 5, wherein said fungal cell is *Aspergillus niger* or *Hansenula polymorphs*.

7. A method according to claim 1, wherein said protein is an enzyme.

8. A method according to claim 1, wherein the host cell is cultured under batch, fed-batch, or continuous fermentation conditions.

9. A method according to claim 1, wherein said protein is native to said host cell.

10. A method according to claim 1, wherein said protein is heterologous to said host cell.

11. A method according to claim 1, wherein said protein is secreted into the culture medium, and wherein the method further comprises recovery of the protein from the culture medium.

* * * * *